(12) United States Patent
Valducci et al.

(10) Patent No.: US 6,994,873 B2
(45) Date of Patent: Feb. 7, 2006

(54) MULTIPARTICULATE FORMULATIONS OF LITHIUM SALTS FOR ORAL ADMINISTRATION SUITABLE FOR ONCE-A-DAY ADMINISTRATION

(75) Inventors: Roberto Valducci, Savignano Sul Rubicone (IT); Tiziano Alighieri, Rimini (IT); Serozh Avanessian, Rimini (IT)

(73) Assignee: Valpharma S.A., Serravalle (SM)

( * ) Notice: Subject to any disclaimer, the term of this patent is extended or adjusted under 35 U.S.C. 154(b) by 0 days.

(21) Appl. No.: 10/067,624

(22) Filed: Feb. 4, 2002

(65) Prior Publication Data

US 2002/0172727 A1 Nov. 21, 2002

(30) Foreign Application Priority Data

Feb. 5, 2001 (IT) ..................... MI2001A0220

(51) Int. Cl.
| | |
|---|---|
| A61K 33/00 | (2006.01) |
| A61K 33/14 | (2006.01) |
| A61K 31/19 | (2006.01) |
| A61K 31/198 | (2006.01) |
| A61K 9/00 | (2006.01) |
| A61K 9/14 | (2006.01) |
| A61K 9/22 | (2006.01) |
| A61K 9/52 | (2006.01) |

(52) U.S. Cl. ........................ 424/715; 424/458; 424/459; 424/460; 424/461; 424/462; 424/464; 424/465; 424/468; 424/469; 424/470; 424/474; 424/475; 424/476; 424/477; 424/478; 424/479; 424/480; 424/481; 424/482; 424/489; 424/490; 424/491; 424/492; 424/493; 424/494; 424/495; 424/496; 424/497; 424/498; 424/499; 424/500; 424/501; 424/502; 424/677; 424/709; 424/711; 424/717; 424/722; 514/553; 514/557; 514/558; 514/560; 514/574; 514/769; 514/772.3; 514/773; 514/781; 514/951; 514/964; 514/561

(58) Field of Classification Search ................ 424/464, 424/465, 468–470, 474–482, 489–502, 677, 424/715, 717, 722, 458–462, 709, 711; 514/553, 514/557, 558, 560, 561, 574, 769, 772.3, 514/773, 781, 951, 964
See application file for complete search history.

(56) References Cited

U.S. PATENT DOCUMENTS

2004/0013746 A1 * 1/2004 Tarro .......................... 424/715
2004/0241252 A1 * 12/2004 Abney et al. ................ 424/715

FOREIGN PATENT DOCUMENTS

| EP | 0052075 A | 5/1982 |
|---|---|---|
| EP | 0396425 A | 11/1990 |
| FR | 2244485 | 4/1975 |

OTHER PUBLICATIONS

Degussa, Rohm Pharma Polymers, Product Information: "Scientific Names According to IUPAC Regulations," Aug. 1999.*
Gai, M.N. et al., "Evaluation of the in vitro and in vivo performance of two sustained–release lithium carbonate matrix tablets. Effect of different diets on the bioavailability," Drug Development and Industrial Pharmacy, vol. 25(2), 1999, pp. 131–140.*
Rafiee–Tehrani, Morteza, et al, Formulation of Controlled Release Lithium Carbonate Tablets by Fluid Bed Technique, Eur. J. Pharm. Biopharm., 39 (2)1993, pp. 87–91.

* cited by examiner

Primary Examiner—John Pak
(74) Attorney, Agent, or Firm—William J. Sapone; Coleman Sudol Sapone PC

(57) ABSTRACT

This invention refers to:
multiparticulate formulations of Lithium salts for oral administration constituted by either modified release granules or mixtures of modified and conventional release granules, suitable for once-a-day administration also at high strengths of Lithium salts,
and to the preparation process of said formulations.

8 Claims, No Drawings

MULTIPARTICULATE FORMULATIONS OF LITHIUM SALTS FOR ORAL ADMINISTRATION SUITABLE FOR ONCE-A-DAY ADMINISTRATION

TECHNICAL FIELD

This invention refers to multiparticulate formulations constituted by either modified release granules of Lithium salt or mixtures of modified and conventional release granules; particularly, it refers to formulations suitable for the once-a-day administration.

BACKGROUND ART

Lithium salts, in particular Lithium Carbonate, are widely utilized for the prophylaxis and the treatment of mania, maniacal depression, bipolar mania and unipolar mania. The conventional formulations of Lithium salts cause a rapid gastroenteric absorption, which determines the necessity of repeated dosings during the day.

Furthermore, in planning formulations containing Lithium, it has to be borne in mind that the margin between the therapeutic concentration and the toxic concentration is very small and the side effects reported during the therapy are often due to the overcoming of the toxic dose, in particular in sensitive patients and in elderly people.

Several techniques are described allowing the obtainment of Lithium salt formulations for the above stated psychiatric treatments. For example, patent EP 0222 411 B1 allows to obtain a multiparticulate formulation suitable for Lithium salt administration, but it has to use saccharose crystals for the formation of particles containing Lithium salt, with the consequence that the obtainable dosages are low.

Moreover, for the particle coating, fats with low melting points have to be used, which limits the dissolution characteristics.

U.S. Pat. No. 5,445,829 allows to prepare prolonged release multiparticulates, but requires, anyway, the use of a core or inert substratum to carry the drug and, therefore, the obtainable formulations are not suitable for high dosages of the active ingredient.

To obtain suitable dosages for the Lithium therapy, i.e. 0.4–1.2 g/day in the prophylaxis and up to 2 g/day in the acute treatment of states of mania, the use of tablet formulations is frequent. We cite, for example, the formulation referred to in U.S. Pat. No. 4,264,573, in which the Lithium Carbonate content is high (70–80%), but the disadvantage is represented by the monolithic form. The patent EP 471 100 describes controlled release tablets obtained through the matrix technique, having 400 mg of Lithium Carbonate per tablet. Said tablets have the disadvantage of a too low dosage for the most of the therapeutic purposes; additionally, they exhibit the same disadvantages of the monolithic forms.

SUMMARY OF THE INVENTION

It has been now found a multiparticulate formulation of Lithium salts, based on microgranules or micro-tablets, for once-a-day administration, which allows to overcome the disadvantages of the prior art.

Such formulation is constituted by either modified release granules or mixtures of modified and conventional release granules, having dimensions ranging from 200 to 2000 micrometers and a Lithium salt content, expressed as Lithium Carbonate, of at least 500 mg/g, suitable for strengths up to 1000 mg/dose.

The procedure for the preparation of said formulation includes:

a) the granulation of the Lithium salt in powder form by means of a solution of a binder agent;

b) the sieving of the granules obtained in stage a) ranging between 200 and 2000 micrometers with the obtainment of conventional release formulations;

c) the coating of all or part of the granules obtained in stage b) with the aim of obtaining modified release formulations.

Said formulations can be prepared in form of microgranules or micro-tablets.

DESCRIPTION OF THE INVENTION

This invention refers to multiparticulate formulations constituted by either modified release granules of Lithium salt or mixtures of modified and conventional release granules; particularly, it refers to formulations suitable for the once-a-day administration.

Said formulations have a Lithium salt content of at least 500 mg/g and, preferably, of at least 900 mg/g expressed as Lithium Carbonate.

The modified release forms allow a gradual release in the 24 hours.

The procedure for the preparation of the formulations according to this invention includes:

a) the granulation of the Lithium salt in powder form by means of a solution of a binder agent chosen from the group including polyvinylpyrrolidone, polyethyleneglycol, saccharose and gelatin;

b) the sieving of the granules obtained in stage a) ranging between 200 and 2000 micrometers with the obtainment of conventional release formulations;

c) the coating of all or part of the granules obtained in stage b) with the aim of obtaining modified release formulations.

Said formulations can be prepared in form of microgranules or micro-tablets. The granulation of stage a) can be realized utilizing known equipment like a fluidized bed, a rotating granulator or an extruder.

In case of the rotating granulator, the preparation can be completed in a rotating pan and, in case of the extruder, the preparation can be completed through spheronization.

The starting Lithium salt powder has a granulometry lower than 100 micrometers.

The Lithium salt is chosen from the group including Lithium Carbonate, acetate, glutamate, thionate and sulphate.

The solution of the binder agent can be an aqueous solution or an organic solvent solution. Among the organic solvents ethanol is the preferred one. Among the binder agents the preference is for polyvinylpyrrolidone.

The solution of the binder agent has a concentration ranging from 3% to 20%. The quantity of binder utilized in the granulation ranges from 0.5% to 15% compared to the Lithium salt.

From the product obtained through the granulation, the granules ranging from 200 to 2000 micrometers are selected through sieving.

The granules obtained from stage a) and b) show a conventional unmodified release, as they are free from coating with agents suitable for modifying the dissolution speed.

The coating of stage c), generally, is realized through the fluid bed technique. The substances utilized for the coating are chosen from the group including derivatives and polymers of acrylic and metacrylic acid, cellulose derivatives, stearic acid, paraffin, natural polymers like shellac, zein, or mixtures of the same in any proportion, charged, if necessary, with therapeutically acceptable plasticizer agents.

The derivatives and the polymers of acrylic and metacrylic acid are preferably chosen among Eudragit L®, Eudragit RS® and Eudragit RL®.

The scientific names according to IUPAC regulations for these materials are as follows: Eudragit L-poly (methacrylic acid-co-methyl-methacrylate, 1:1, 135,000 MW (L 12, 5, L 100) or poly (methacrylic acid-co-ethyl acrylate) 1:1, 250,000 MW (L 30 D-55, L 100-55); Eudragit RS-poly (ethyl acrylate-co-methyl methacrylate-co-trimethyl ammonioethyl methacrylate chloride) 1:2:0.1; 150,000 MW; Eudragit RL poly (ethyl acrylate-co-methyl methacrylate-co-trimethyl ammonio ethyl metacrylate chloride) 1:2:0.2, 150,000 MW.

The cellulose derivatives are preferably chosen among, ethylcellulose, hydroxypropylmethylcellulose, hydroxypropylmethylcellulosephtalate and celluloseacetatephtalate.

Opportunely varying the type and the quantity of the coating substances, formulations exhibiting various dissolution profiles are obtained, including a variety of forms suitable for the oral administration.

The formulations according to this invention preferably have an in vitro dissolution profile as per the following table:

| HOURS | % OF DISSOLVED LITHIUM CARBONATE |
|---|---|
| 1 | 5–25 |
| 4 | 20–55 |
| 8 | 40–80 |
| 12 | 60–90 |
| 16 | >75 |
| 24 | >80 | or:

| HOURS | % OF DISSOLVED LITHIUM CARBONATE |
|---|---|
| 1 | 5–25 |
| 4 | 20–45 |
| 8 | 40–65 |
| 12 | 50–80 |
| 16 | 60–90 |
| 24 | >90 |

Acting according to this invention it is possible to obtain gastroresistant formulations, retard formulations and pH-sensitive formulations. Furthermore, it is possible to prepare formulations constituted by mixtures of conventional release multiparticulates, obtained as per stage b), and modified release multiparticulates, as per stage c), in any proportion.

The formulations according to this invention can be prepared in form of microgranules, pellets, spheroids and micro-tablets, that can be dosed into gelatin capsules, sachets and granulate dispensers or, otherwise, can be pressed to obtain rapidly disgregating tablets releasing the multiparticulate.

The formulations according to this invention show the advantages of the multiparticulate preparations characterized by uniformity of the gastroenteric transit times and wide distribution of the particles carrying the active ingredient in the intestinal lumen, with better absorption and, therefore, more homogeneous responses to the pharmacological therapy.

For a better explanation of the invention the following examples are reported.

EXAMPLE N° 1

4.5 Kg of Lithium Carbonate in powder form having granulometry lower than 100 micrometers were granulated in a fluid bed apparatus provided with a tangential spray insert.

For the granulation, a mixture constituted by:

600 g of an ethanolic solution of polyvinylpyrrolidone at 5%;

2100 g of ethanol;

was fed in the fluid bed.

The granulation was carried out at a temperature of about 25° C.

Spherical granules were obtained and selected by sieving in order to collect the particles ranging between 700 and 1000 micrometers.

1.1.

1 Kg of granules obtained from example N°. 1 was coated in fluid bed with Bottom spray insert with 500 g of solution of ethylcellulose 5% in ethanol. The obtained multiparticulate was checked to evaluate the strength of the active ingredient and the dissolution profile by Basket Apparatus, EP-USP.

| RELEASE | | | | | | POTENCY Content in |
|---|---|---|---|---|---|---|
| 1 h | 4 h | 8 h | 12 h | 16 h | 24 h | mg/g |
| 10% | 28% | 53% | 63% | 76% | 82% | 950 |

1.2.

1 Kg of granules of example N° 1 was coated, utilizing a fluid bed equipment with Bottom spray system, with the following solution:

| Eudragit L 10% in ethanol | 400 g |
|---|---|
| Ethanol | 320 g |
| Diethylphtalate | 8 g |

The so obtained granules were tested to verify the gastroresistance, obtaining the following results:

| HOURS | | RELEASE |
|---|---|---|
| 1 h | HCl 0,1 N | 0% |
| 2 h | | 2% |
| 1 h | Buffer at pH 6.8 | 95% |

These results show that the granules of example N° 1.2. are grastroresistant while they dissolve at the intestinal pH value.

1.3.

1 Kg of granules of example N° 1 was processed as per example N° 1.1., but with the following solution:

| | |
|---|---|
| Hydroxypropylmethylcellulose-P50 (HPMCP–50) 5% in acetone | 700 g |
| Diethylphtalate | 7 g |

The obtained results are superimposable to those of example N° 1.1.

EXAMPLE N° 2

2 Kg of Lithium Carbonate in powder having granulometry lower than 100 micrometers were put into fluid bed apparatus equipped with tangential insert. The multiparticulate formation was obtained feeding the fluid bed with 900 g of 10% ethanolic solution of polyvinylpyrrolidone. From the obtained granules, the fraction having granulometry ranging from 400 to 800 micrometers was selected. On 1 Kg of these granules, 2 Kg of Lithium Carbonate powder were applied through the fluid bed technique (as in the first stage, polyvinylpyrrolidone 10% in ethanol was utilized as binder).

2.1.

On 700 g of granules of example N° 2, through the fluid bed technique, 2 Kg of Lithium Carbonate in suspension with the following composition were applied:

| | |
|---|---|
| Lithium Carbonate | 2.0 Kg |
| Polyvinylpyrrolidone 10% in ethanol | 1.0 Kg |
| Ethanol | 2.5 Kg |
| Water | 1.0 Kg |

The so obtained granules (spheroidal multiparticulate) were coated through the fluid bed technique with quantities similar to what reported in example N° 1.1., utilizing a solution of ethylcellulose 5% in ethanol. The analytical controls to evaluate the dissolution profile and the strength were carried out utilizing the previously mentioned methods and apparatus.

The results are superimposable to those of example N° 1.1.

EXAMPLE N° 3

8 Kg of Lithium Carbonate in powder having granulometry lower than 100 micrometers were granulated by means of a Viani granulator model ST 25, utilizing 1.8 Kg of a solution of polyvinylpyrrolidone 5% in water. The wet mass was forced through a net of 1000 µm and, after desiccation of the multiparticulate, the granules ranging from 400 to 800 µm were selected. 3 Kg of the so obtained granules were transferred into a rotating pan, where 2 Kg of Lithium Carbonate were applied; 600 g of solution of polyvinylpyrrolidone 10% in ethanol were utilized as binder.

3.1.

4 Kg of granules obtained from example N° 3 were coated several times in a fluid bed apparatus for a total of 2.5 Kg of solution of ethylcellulose 5% in ethanol. The results of the tests carried out are the following:

| RELEASE | | | | | | POTENCY Content in |
|---|---|---|---|---|---|---|
| 1 h | 4 h | 8 h | 12 h | 16 h | 24 h | mg/g |
| 14.3% | 49.4% | 65% | 76% | 85% | 98% | 940 |

3.2.

1 Kg of granules obtained from example N° 3 were coated in fluid bed with Bottom spray system utilizing 500 g of a solution of ethylcellulose 5% in ethanol; the final granules gave the following results:

| RELEASE | | | | | | POTENCY Content in |
|---|---|---|---|---|---|---|
| 1 h | 4 h | 8 h | 12 h | 16 h | 24 h | mg/g |
| 12% | 26% | 48% | 68% | 80% | 92% | 956 |

3.3.

3 Kg of granules of example N° 3 were mixed with 15 g of magnesium stearate and the mixture was pressed with punches of diameter of 2 mm. Micro-tablets having an height of 1.5 mm and an average weight of about 22 mg were obtained.

3.4.

1 Kg of micro-tablets obtained as per example N° 3.3. was coated with ethylcellulose in a fluid bed apparatus utilizing the following mixture:

| | |
|---|---|
| Solution of ethylcellulose 5% in ethanol | 300 g |
| Diethylphtalate | 3 g |
| Talc | 5 g |

The so obtained micro-tablets were tested giving the following results:

| RELEASE | | | | | |
|---|---|---|---|---|---|
| 1 h | 4 h | 8 h | 12 h | 16 h | 24 h |
| 7% | 21% | 47% | 60% | 81% | 91% |

3.5.

1 Kg of micro-tablets obtained as per example N° 3.3. was coated, in the same conditions of the preceding example, utilizing the following mixture:

| | |
|---|---|
| Eudragit L 30D ® | 150 g |
| Talc | 20 g |
| Peg 4000 | 7 g |
| Water | 300 g |

The micro-tablets were tested to evaluate their gastroresistance obtaining the following results:

| HOURS | | RELEASE |
| --- | --- | --- |
| 1 h | HCl 0,1 N | 0% |
| 2 h | | 0% |
| 1 h | Buffer at pH 6.8 | 87% |

EXAMPLE N° 4

8 Kg of Lithium Carbonate in powder having granulometry lower than 100 micrometers were mixed with 2 Kg of a solution of polyvinylpyrrolidone 10% in ethanol and forced by means of an extruder; the so obtained granules were transferred into a spheronizer and let turn at 700 r.p.m. obtaining a spheroidal multiparticulate of diameter ranging from 800 to 1000 micrometers.

4.1.

1 Kg of the so obtained granules was coated in a fluid bed apparatus with 500 g of a solution of ethylcellulose 5% in acetone with the following results:

| RELEASE | | | | | | POTENCY Content in |
| --- | --- | --- | --- | --- | --- | --- |
| 1 h | 4 h | 8 h | 12 h | 16 h | 24 h | mg/g |
| 14% | 41% | 64% | 75 | 80% | 93% | 959 |

4.2.

1 Kg of granules of example N° 4 was coated in a fluid bed apparatus with 300 g of a solution of Eudragit RS 10% in acetone plasticized with 6 g of diethylphtalate. The testing of the product gave the following results:

| RELEASE | | | | | | POTENCY Content in |
| --- | --- | --- | --- | --- | --- | --- |
| 1 h | 4 h | 8 h | 12 h | 16 h | 24 h | mg/g |
| 15% | 50% | 75% | 84% | 92% | 100% | 924 |

4.3.

1 Kg of granules of example N° 4 was coated in a fluid bed apparatus with Bottom spray system with the following solution:

| Eudragit RS ® 10% in acetone | 350 g |
| --- | --- |
| Eudragit RL ® 10% in acetone | 40 g |
| Ethanol | 400 g |
| Talc | 10 g |
| Diethylphtalate | 8 g |

The so obtained granules were tested obtaining the following results:

| RELEASE | | | | | | POTENCY Content in |
| --- | --- | --- | --- | --- | --- | --- |
| 1 h | 4 h | 8 h | 12 h | 16 h | 24 h | mg/g |
| 18% | 54% | 76% | 89% | 100% | — | 914 |

4.4.

1 Kg of granules of example N° 4 was coated as per example N° 4.2. with the following substances:

| Eudragit NE 30D | 167 g |
| --- | --- |
| Talc | 50 g |
| Water | 185 g |

The granules were tested obtaining the following results:

| RELEASE | | | | | | POTENCY Content in |
| --- | --- | --- | --- | --- | --- | --- |
| 1 h | 4 h | 8 h | 12 h | 16 h | 24 h | mg/g |
| 9% | 37% | 61% | 72% | 86% | 93% | 870 |

4.5.

1 Kg of granules of example N° 4 was coated as per example N° 4.2. with the following solution:

| Solution of ethylcellulose 5% in ethanol | 400 g |
| --- | --- |
| Stearic acid | 2 g |
| Ethanol | 200 g |

The so obtained granules were tested giving the following results:

| RELEASE | | | | | | POTENCY Content in |
| --- | --- | --- | --- | --- | --- | --- |
| 1 h | 4 h | 8 h | 12 h | 16 h | 24 h | mg/g |
| 10.4% | 28.6% | 53.2% | 63.7% | 76.2% | 82.3% | 950 |

4.6.

1 Kg of granules of example N° 4 was coated as per example N° 4.2. with the following composition:

| Eudragit RS 10% in acetone | 290 g |
| --- | --- |
| Stearic acid | 10 g |

The so obtained granules gave the following results:

| RELEASE | | | | | | POTENCY Content in |
|---|---|---|---|---|---|---|
| 1 h | 4 h | 8 h | 12 h | 16 h | 24 h | mg/g |
| 13% | 42% | 69% | 81% | 94% | 100% | 930 |

All the examples carried out allow the filling of capsules of different sizes, obtaining dosages of Lithium Carbonate ranging from 50 to 800 mg/capsule; the capsules submitted to the analytical controls give results superimposable to those of the multiparticulates and the dissolution profile does not vary with the variation of the dosage.

Finally, it is possible to dose into a capsule any proportion of granules with various modified or conventional release dissolution typologies, allowing, on the base of the clinical evaluation, a wide variety of posology regimens.

Utilizing the micro-tablets described in example N° 3.2 and/or 3.3. it is moreover possible to elevate the quantity dosed into a capsule up to 1000 mg of Lithium Carbonate.

The clinical trials have confirmed the possibility to utilize the formulations of this invention for once-a-day administration, maintaining pharmacological levels up to 24 hours.

What is claimed is:

1. A multiparticulate formulation comprising plurality of microgranules or microtablets having dimensions ranging from 200 to 2000 micrometers, wherein each microgranule or microtablet consists essentially of lithium salts and a binder agent and is obtained by granulating the lithium salts with a solution of the binder agent, said plurality of microgranules or micro-tablets being a mixture containing microgranules or microtablets that are coated to have modified release and a remaining portion being uncoated microgranules or microtablets having an unmodified release, said formulation having a lithium salt content of at least 500 mg/g and said mixture having sufficient modified release coated microgranules or microtablets to have an in vitro dissolution profile suitable for once-a-day administration.

2. The formulation according to claim 1, wherein said Lithium salt content is at least 900 mg/g.

3. The formulation according to claim 1, wherein said Lithium salt is selected from the group consisting of lithium carbonate, acetate, glutamate, thionate and sulphate.

4. The formulation according to claim 1, wherein the modified release microgranules or microtablets are coated with a substance selected from the group consisting of polymers of acrylic and methacrylic acid, cellulose derivatives, stearic acid, paraffin, shellac, zein, and mixtures of the same in any proportion, optionally charged with therapeutically acceptable plasticizers.

5. The formulation according to claim 4, wherein said polymers of acrylic and methacrylic acid are selected from the group consisting of poly (methacrylic acid-co-ethyl acrylate), 1:1, 250,000 MW, poly (ethyl acrylate-co-methyl methacrylate-co-trimethyl ammonioethyl methacrylate chloride), 1:2:0.1, 150,000 MW, and poly (ethyl acrylate-co-methyl methacrylate-co-trimethyl ammonioethyl methacrylate chloride), 1:2:0.2, 150,000 MW.

6. The formulation according to claim 4, wherein said cellulose derivatives are selected from the group consisting of ethylcellulose, hydroxypropylmethylcellulose, hydroxypropylmethylcellulosephtalate, and celluloseacetatephtalate.

7. The formulation according to claim 4, wherein the formulation contains uncoated microgranules and coated microgranules.

8. The formulation according to claim 1, wherein the formulation mixture has coated an amount of modified release microgranules or microtablets and an amount of unmodified release microgranules or microtablets sufficient to have a dissolution profile where from 5–25% of the Lithium salt is dissolved in one hour, 20–45% is dissolved in four hours, 40–65% is dissolved in eight hours, 50–80% is dissolved in twelve hours; and 60–90% is dissolved in twenty-four hours.

* * * * *